United States Patent [19]

Eisenmenger

[11] Patent Number: 4,669,472

[45] Date of Patent: Jun. 2, 1987

[54] CONTACTLESS COMMINUTION OF CONCREMENTS IN THE BODY OF A LIVING BEING

[75] Inventor: Wolfgang Eisenmenger, Landhausstrasse 7, 7140 Ludwigsburg, Fed. Rep. of Germany

[73] Assignee: Wolfgang Eisenmenger, Ludwigsburg, Fed. Rep. of Germany

[21] Appl. No.: 802,720

[22] Filed: Nov. 27, 1985

[30] Foreign Application Priority Data

Nov. 28, 1984 [DE] Fed. Rep. of Germany ....... 3443295

[51] Int. Cl.⁴ .................................................. A61B 17/22
[52] U.S. Cl. .................................. 128/328; 128/24 A
[58] Field of Search ....................... 128/328, 24 A, 660

[56] References Cited

U.S. PATENT DOCUMENTS 4,311,147  1/1982  Hausler ............................... 128/328

FOREIGN PATENT DOCUMENTS 3312014 10/1984 Fed. Rep. of Germany ...... 128/328
2140693 12/1984 United Kingdom ................. 128/328

Primary Examiner—Clifford D. Crowder
Attorney, Agent, or Firm—Ralf H. Siegemund

[57] ABSTRACT

A device for contactless comminution of concrements in the body of living beings includes a casing with a hollow interior filled with a shock wave transmitting medium; the internal surface configuration is spherically-calotte shaped serving as support for an electric coil covered by insulation which in turn supports a metallic membrane of spherically-calotte shaped configuration, in addition the cavity has a boundary configured as a truncated cone, the apex of the cone coincides with the center of curvature of the membrane. The cavity content is under compression (liquid or solid) and is closed by a coupling member to be placed in abutment with the body of the human being, this coupling member may shift the focal point of the shock waves.

13 Claims, 3 Drawing Figures

CONTACTLESS COMMINUTION OF CONCREMENTS IN THE BODY OF A LIVING BEING

BACKGROUND OF THE INVENTION

The present invention relates to the contactless comminution of concrements in the body of a living being particularly to the destruction and disintegration of kidney stones in human beings. More particularly the invention relates to equipment of the aforementioned type having a spherical-calotte shaped metal membrane the outwardly curved surfaces of which being juxtaposed to at least one coil but separated therefrom by means of an electrical insulation, and the concavely curved inwardly oriented surface is in contact with an acoustic transmission medium such as a liquid; the coil is energizable by means of electric currents to cause repulsion of the metal membrane so that as a consequence a shock wave is transmitted into the transmission medium and propagates towards the concrement whereby on account of the focusing action of the curvature of the membrane shock wave energy is concentrated into the concrement.

Generally speaking a device of the type to which the invention pertains is shown in my German printed patent application No. 33 12 014. The device disclosed in this application has particular advantages and constitutes a certain progression over an earlier state of the art for contactfree comminution of concrements using underwater sparks or ultrasonic generation. This particular printed patent application describes in detail the earlier state of the art. The particular device suggested by this German patent application has the advantage of simplified construction, a high use life, a high degree of reliability and particularly it excludes certain risks for the general state of health of the patient. Moreover the device disclosed in this application permits avoiding utilization of liquid bath into which the patient has to be submerged and is easier adjustable as compared with the prior art structures and offers more reliably reproducible results.

As far as particulars are concerned printed patent application No. 33 12 014 discloses a conductor arrangement having inductive properties and includes a spirally shaped coil or a coil wound under utilization of a ribbon conductor. This coil configuration has also the shape of a spherical calotte. Upon feeding a current pulse into the coil, e.g. through discharge of a capacitor and connecting it in series with a spark gap opposing currents are induced in a metal membrane being separated from the coil through a thin electrically insulated layer which opposing currents cause in fact a repulsion of the membrane. As an alternative source for electric current a high power generator could be used to feed a current pulse into the coil with the same result as far as membrane action is concerned. Since the membrane is in contact with the transmission medium shock waves are produced and emitted, and on account of the spherical-calotte shaped configuration of the membrane these shock waves are in fact focused e.g. into a kidney stone.

DESCRIPTION OF THE INVENTION

It is an object of the present invention to provide a new and improved device for the comminution of concrements in living beings and using as a point of departure the state of the art as disclosed in German printed patent application No. 33 12 014 with the intention being to improve focusing and other aspects.

It is a particular object of the present invention to provide a new and improved device for contact less comminution of concrements in the body of living beings, including a casing with a hollow interior filled with a shock wave transmitting medium and wherein an internal surface has a spherical-calotte shaped curvature and serves as support for an electric coil there being a correspondingly curved insulation on the coil, and a metallic membrane also of spherical-calotte shaped configuration is held on said insulation layer, additionally there are means for providing an electric current pulse or pulses to the coil.

In accordance with the preferred embodiment of the present invention it is suggested to provide on the side of the metal membrane constituting the focusing and shock wave producing surface a construction part which surrounds a cavity and has the contour of a truncated cone whereby the larger end faces the membrane and the smaller end of the cone faces the concrement to be comminuted and of course contains in the transmission medium. The apex of that cone coincides with the center of the concentric spheres, delineated by the insulation and the membrane. This configuration of the part enveloping so to speak the immediate propagation path for shock wave avoids of diffraction and reflection of shock waves which would have undesired parasitic side effects. Such diffraction and refraction occurs in the device of the German printed patent application No. 33 12 014 particularly at casing parts adjacent to the metal membrane. These diffractions and reflections interfere with the formation of a focused wave and produce quasi-focused shock waves which may be concentrated to some extent in tissue adjacent to the concrement to be comminuted. Therefore the inventive feature improves the focusing action of the device as per the particular object which in turn means that the energy density in the focal point is higher than before to thereby increase the efficiency of the device without supplemental features.

The truncated contour of the conical cavity forces a concentric wave propagation in the direction towards the focus in a manner that covers a wide range of frequences. Consequently the energy necessary for developing the initial shock wave in the first place, including particularly the electrical energy used in the capacitor discharge or in the high output power generator, can be smaller than before. This means that the device is simpler and more economical with the same result as far as shock wave concentration is concerned. An important aspect here is that steepness of the leading edge of the pressure pulse to be produced becomes less critical; the onset of a pressure pulse generation (membrane deflection) does not have to be as steep as was previously thought necessary without detrimental effect in the final result. Consequently the particular pulse source which produces the initial current pulse can be much simpler and its layout is less critical for reasons that an excessive steepness of the pulse does not have to be observed. Finally it was found that the wavefront of the shock wave as far as its overall contour is concerned is quite improved which is of great advantage for the shock wave effect in the instant of concrement comminution.

Another important improvement of the focusing effect results from the fact that the construction part having the truncated conelike cavity should be made of a material which has a high acoustic impedance. This is true e.g. for many metals and is particularly so for stainless steel. This feature in turn improves the focusing effect further because the shock waves are, so to speak, guided inside of the truncated cone. It has to be observed that the shock waves are spherical waves as far as propagation is concerned. Moreover the configuration as such, including the choice of the material as proposed here, causes the effective shock wavefront to have a higher steepness as it propagates into the medium. This of course is an aspect permitting the energization process and shock wave initiation to be less critical as far as onset steepness is concerned. The particular part having the truncated conelike cavity may be made entirely of such a material with high acoustic resistance, but it was found that it is sufficient if as such the part is made of any kind of material and the critical material is used only as a lining for the cavity.

It was found to be of advantage if the transmission medium has strongly non-linear compression characteristics. This feature has already been mentioned in the above identified German application No. 33 12 014 but in connection with the present invention this feature opens up possibilities not envisioned in the earlier publication. Involved presently is a shortening of the transition path for purposes of better forming the wavefront of the shock wave. This feature in turn permits reduction in the depth (axially) of the hollow truncated cone. A transmission medium most suitable here for the intended purpose is a liquid such as a halogen hydrocarbon or a material with a modulus of shear or torsion such as a rubber elastic element.

In furtherance of the invention it is suggested to provide a particular coupling structure or member between the transmission medium on one hand and the tissue of the living being on the other hand. This coupling structure or member is to include a material having a relatively low modulus of shear or torsion and is particularly comprised of a rubber elastic member or element or of a liquid which acts in an elastic fashion. The coupling structure or member permits a free propagation of shock waves just as is the case in the tissue; this free propagation becomes particularly effective after a shock wavefront has already been formed pursuant to propagation of the shock waves within the hollow truncated conelike cavity. The reasons for the formation of a shock wavefront in that cavity has been mentioned earlier. The acoustic properties of the coupling structure or member including particularly the acoustic wave impedance and speed as well as the shape of that member are chosen to obtain optimum transition at minimum resistance of the shock wave into the adjoining tissue.

This particular coupling structure or member offers additional advantages. The coupling structure or member can be configured so that the focal point of the shock waves depending upon the particular instance and case of application, shifted farther away or close. A shift of the focal point is thus made possible through this coupling structure itself. The coupling structure or member being configured in the stated manner can also be interpreted as a fine-tuning-like focusing medium. This fine focusing can be obtained particularly through appropriately shaping the outer boundary of the coupling structure. Alternatively a selective variation of the type of material of which the coupling structure is composed is a feature that serves as parameter selection by means of which fine focusing can be obtained. The desired effect can be particularly effectively obtained whenever the coupling structure is provided with a surface of rotational symmetry with a hyperboloid configuration. Involved here particularly is the surface facing the transmission medium. Alternatively that particular surface facing the transmission medium can be configured that any focusing errors as they may occur pursuant to the transition between coupling medium and tissue are compensated therewith. The variation of the focal point as far as its location is concerned is strongly related to the possibility of varying the pulse duration in the focus, a further parameter here is the aperture angle out of the cone and into the coupling member.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood fromthe following description taken in connection with the accompanying drawings in which:

Proceeding now to the detailed description of the drawings FIG. 1 illustrates a first embodiment for practicing the invention and herein reference numeral 1 refers to an equipment case which is composed of two parts, 1a and 1b. The casing part 1a has generally on one side (which is an inside surface of the case as such) a spherically curved calotte like surface configuration which includes a correspondingly contoured coil 2 being in fact inserted in a correspondingly configured indent or flat recess 1a' of the casing part 1a. This coil 2 is comprised basically of a spirally coiled wire, e.g. copper wire. The indent or recess 1a' as it contains the coil 2, is so to speak closed by a relative thin insulating layer, foil or sheathing 3. This layer, foil or cover 3 carries a matchingly contoured metal membrane 4 having therefore a calotte spherically shaped configuration accordingly. Foil 3 and membrane 4 delineate concentric spheres, having a common center 15.

Figure 1:
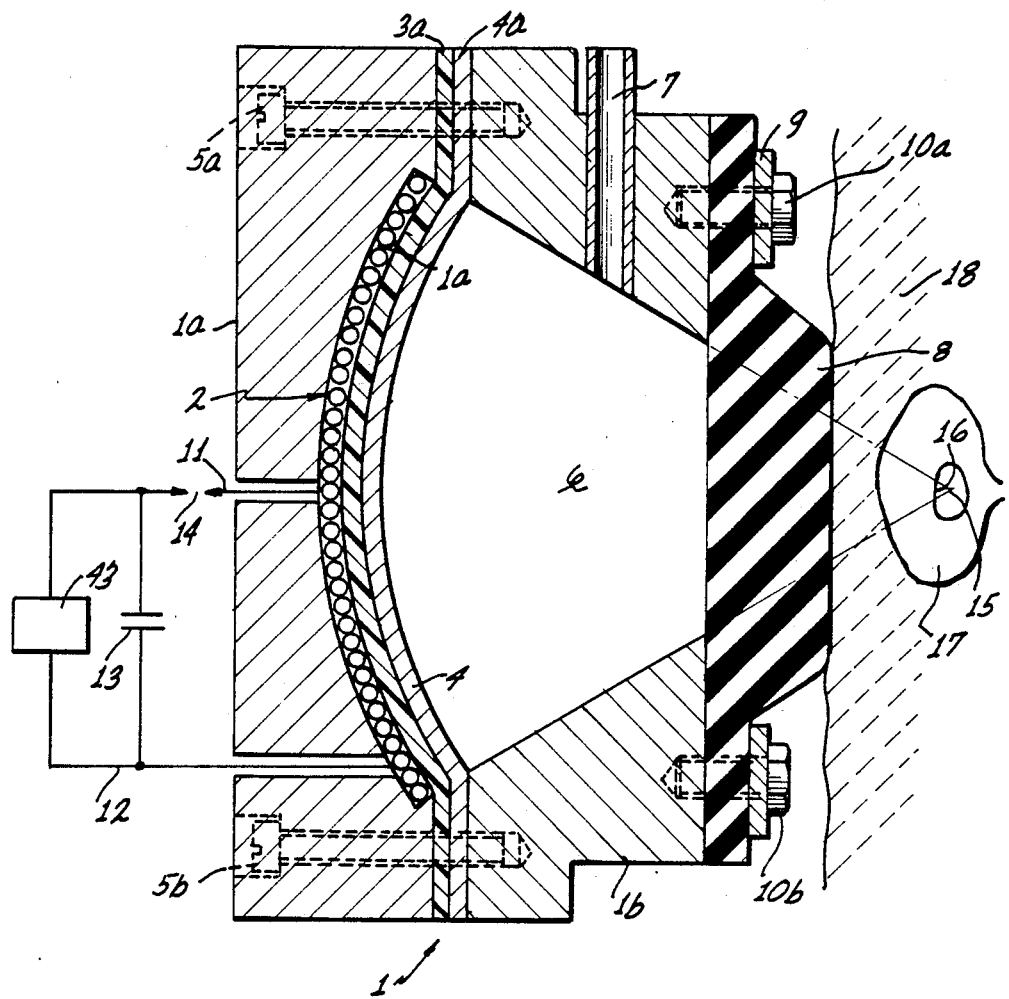
FIG. 1 is a somewhat schematical representation of a section through a device in accordance with the preferred embodiment of the present invention for practicing the best mode thereof under utilization of a transmision medium which is a pressurized liquid.

It should be noted that the thickness dimensions of the elements 3 and 4 are exaggerated. Insulating foil 3 as well as metal membrane 4 are in fact quite thin. They are each provided with radial outer flanges, 3a and 4a respectively by means of which these two elements are sandwiched and clamped in between the casing parts 1a and 1b. Reference numeral 5a and 5b refer to screws which interconnect the two parts 1a and 1b, and the screw connection is therefore directly instrumental for mounting the parts 3 and 4 to the case and for assembling the case from parts 1a, 1b by interconnecting them in this fashion.

The part 1b is provided with a hollow interior, cavity or space 6 having the configuration of a truncated cone. The space 6 is filled with a liquid which for example could be water. The water, however, is pressurized as far as its static pressure is concerned, there being a connection nipple 7 by means of which the interior cavity and here particularly the water content thereof can be connected to a pressure source which provides the pressure PZ being in excess of and above atmospheric pressure.

In lieu of water one may also use another liquid, for instance a halogenic hydrocarbon usually e.g. tetrachlorine carbon. These liquids have an advantage over water in that they exhibit a stronger nonlinear compression characteristics. The nonlinearity being in fact significantly more pronounced than in water. For reasons mentioned above this nonlinearity reduces the propagation path necessary for the formation of a wavefront.

The frustoconical space 6 has a large cross-sectional end and a small cross-sectional end. The small crosslsectional end delineated by a circle having a relatively small radius is provided on the outside of the casing part 1b and adjoins a coupling member 8. In this particular example coupling member 8 is made of a rubber elastic material. This coupling member 8 is bolted to the casing part 1b by means of screws 10a and 10b with additional employment of a fastening ring 9. Generally speaking it is possible to use a hollow coupling element filled with a liquid.

One of the innermost windings of the coil 2 and one of the outermost windings of that coil are respectively connected through conductors 11 and 12 to a source of electrical energy 43. This source will yield pulse shaped electrical currents. In the present example and as a representation of a pulse forming source, a capacitor 13 is provided whose discharge is controlled to run through the coil 2. Connected in series with these elements is a spark gap 14. The source 43 may be controlled to limit the time during which the capacitor 13 can be charged. Upon attaining a particular charge level, gap 14 will fire, and the ensuing discharge of the capacitor produces a pulse through the core 2. Thus the capacitor 13 is regarded as a general representation for a pulse or pulse forming source. Another source such as a controlled high power pulse generator can be used bearing in mind that the coil 2 will become a part also of that source as an effective impedance.

As soon as a current is caused to flow in the coil 2 an eddy current is induced in the metal membrane 4. As a consequence of the current flow in coil 2 and of the induced current in membrane 4 opposing magnetic fields are set up causing the membrane 4 to be repelled from its place of abutment with the insulating foil 3. The force of repulsion depends ultimately on the onset of the current pulse and results in a shock wave being of spherical configuration and being directed inwardly from the membrane towards the focal point which of course is at least in a first approximation geometrically, the center 15 of the sphere delineated by membrane 4 and insulation 3. As a consequence focus shock waves propagate through the frustoconical cavity 6 towards the coupling medium 8. For reasons above and in conjunction with the conical configuration of space 6 the shock wave is guided and directed towards the focal point 15 which is outside of the system and is in fact situated right inside a concrement 16 e.g. a kidney stone located in a kidney 17 of a human patient.

In the instant of launching a pressure pulse by means of the metal membrane and into the medium in cavity 6 this particular pressure pulse does not yet have a steep wavefront. However such a steep front will form during the converging propagation of the pressure wave as produced by the membrane inside of the frustocone as delineated by the interior of part 1b. The particular pressure wave will have a steepness range of about 1 micrometer. The axial depth of the cavity 6 which is the axial height of the truncated cone has to be dimensioned so that the propagation of the shock wave through this space suffices to obtain such a steep wavefront. Thus the axial dimension of the frustocone is proportioned in accordance with this requirement. Clearly if the pressure pulse as produced right at the concave outwardly facing membrane surface is rather steep, the propagation path needed to obtain the requisite ultimate steepness of the pressure wave is shortened. On the other hand it can readily be seen that there is a trade-off here in selecting the cone longer and to provide simplified energization elements i.e. simplified electric circuit that actuates the membrane 4. Moreover, the duration of the shock wave pulse within the focus 15 is subject to a variety of operative parameters. Diffraction could occur at the small end of the frustocone beyond which shock waves are permitted to propagate freely. Diffraction by this fringe area has a certain effect on the duration of the shock wave in the focal point. That duration is subject to modification through appropriate choice of the apex angle of the cone. Specifically for a smaller angle of the cone the pulse duration in the focal point 15 is shortened. This in turn is advantageous for the efficiency of the electromagnetic shock wave generation involving the coil 2, the membrane 4 and the devices that produce the pulse. It was also found that in this manner the comminution process of the concrement, breaking it up is advantageously controlled in this manner toward obtaining very small pieces. One should therefore choose a very small apex angle for the cone.

Generally speaking owing to the truncated conelike configuration of the cavity 6 while the front wave contour of the shock wave is considerably improved the focusing of the generated shock wave is likewise improved. In the absence of this particular truncated cone 6 housing parts along the fringes or edges would produce diffraction and reflection which in turn would produce parasitic shock waves which are no longer focused in 15 but which to some extent may appear to be concentrated and in a highly detrimental fashion may be concentrated into parts of the kidney 17 outside of the stone 16. The frustoconical configuration of cavity 6 in conjunction with the particular mode of producing a shock wave along the extension of the membrane 4 where facing the cavity, has a waveguidelike effect suppressing diffraction and reflection and parasitic waves. This waveguide effect will be enhanced by making the part 1b of a material having a high resistance against shock wave, or, generally, sound and ultrasonic wave transmission. In the preferred form stainless steel is to be used for this part 1b. Alternatively just the surface of part 1b defining the truncated cone may be lined with stainless steel, the remainder of a housing part 1b can be made of a less expensive material. Owing to the favorable formation of the wavefront it is now possible to reduce the energy that is used to generate the shock wave in the first place and including here particularly the amount of electrical energy discharged by the capacitor and the circuit generally which causes a particular onset steepness of the current pulse on initiating the capacitor discharge.

Figure 3:
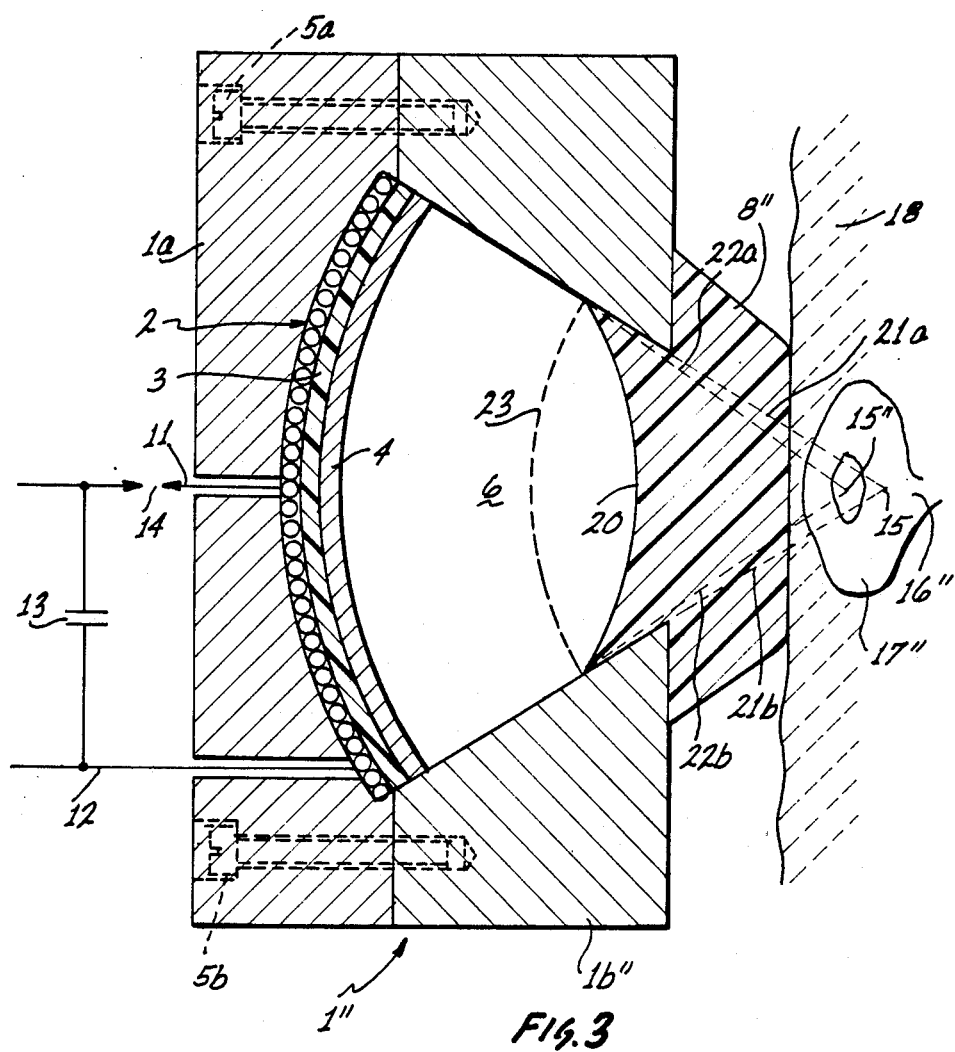
FIG. 3 is a further modification of the inventive structure using a liquid as a transmission medium in combination with a coupling structure having additional properties of shifting the focal point.

The wave as produced and as propagating in cavity 6 will enter the coupling body 8. This body or member 8 has an inside surface which in fact is a boundary or interface with the space 6. Member 8 has an outside surface which abuts the skin tissue 18 of the patient. The shock waves therefore pass through this coupling body or member 8 and into the body 18 of the human patient. The body or member 8 is shown as a solid but basically it could be hollow filled with a particular transmission medium. On the other hand it can be seen that 6 may not be a true cavity but a solid, namely the same solid of which coupling member is made of for purposes of avoiding the 6-8 interface, being no matter how carefully the materials are selected inherently a discontinuity. The coupling member 8 on account of its different acoustic impedance does in fact cause the focal point to be shifted away from the geometric center of the sphere defined by the membrane 4 which is the apex point of the cone. The focal point can be shifted also intentionally if the curvature of the calotte shaped membrane 4 is subject to variation. Further possiblities will be discussed later with reference to FIG. 3 and are somewhat simpler.

Figure 2:
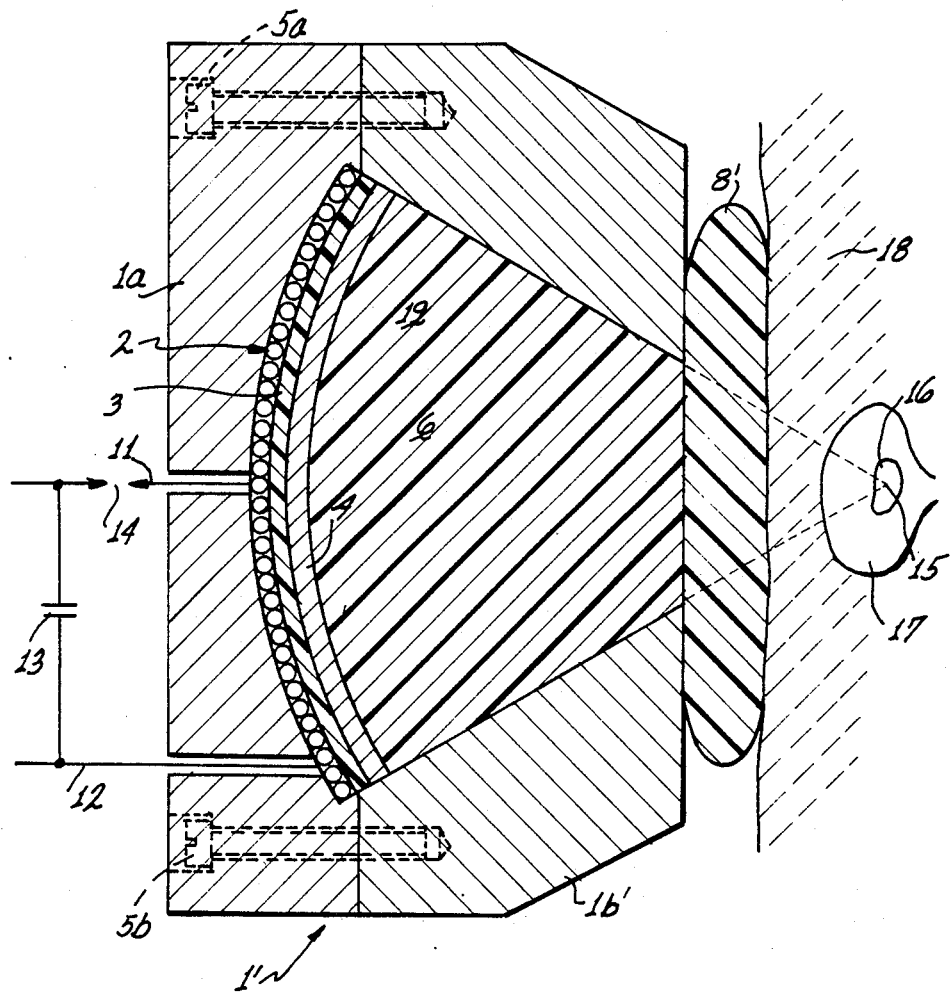
FIG. 2 is a view similar to FIG. 1 but in which in accordance with the modification the transmission medium is constructed as a rubber eleastic body.

A solid filling of cavity 6 is shown in FIG. 2. Parts identified by a "prime" in FIG. 2 correspond generally to parts shown in FIG. 1 as identified therein by numerals without a "prime" but there are differences which are related to certain structural aspects but do not involve principal considerations. The example of FIG. 2 assumes that cavity 6 is not filled by a liquid but by a rubber elastic body 19 which is of frustoconical configuration. This rubber elastic member 19 just as the utilization of a particular liquid in the embodiment of FIG. 1, exhibits a nonlinear compressibility. This nonlinearity shortens the transit path length needed for the formation of a shock wavefront. However, just as in FIG. 1 the rubber elastic body 19 is under pressure. This pressure basiclly results from squeezing an oversize body 19 into the cavity 6, in particular in part 1b' and that compression results in a pressurization of the body 19. This compression bias will remain effective, without utilization of an external pressure source. Reference numeral 8' refers to a coupling element which physically is in contact and engages with one circular end face of the body 19 corresponding to the small diameter of the frustocone. For reasons of generality members 19 and 8' can be made of different material but it is apparent for reasons of avoiding the set up of an acoustic discontinuity it is of advantage to use similar materials for these parts 19 and 8' and possibly they may even be of integral one piece configuration.

FIG. 2 shows another simplification which is made possible in this case, in that the membrane 4 and the insulating stratum 3 do not have to be provided with mounting flanges; the two elements are simply clamped in between the housing path 1a and the solid body 19.

Proceeding now to the description of FIG. 3, again similar reference numerals refer to similar even identical parts are and remain the same as in FIG. 2 or 1 but those parts which merely have certain functional correspondence to parts in FIGS. 2 and 1 are defind by similar reference numeral with two "primes". This embodiment is disclosed here to show the possiblity for varying the focal distance without having to change the outer contour of the metal membrane 4. The transmission medium for the shock waves is a hollow cavity 6 filled with pressurized water or another suitable liquid. For reasons of simplification the pressurization source is not shown in this instance.

The coupling body 8" is configured quite differently from the outer examples; it extends in parts into the part 1b" whereby this insertion merely has stopperlike function; the cavity 6 is just to be closed tightly. The member 8" has an inwardly oriented surface 20 which is configured at a rotational hyperboloid of simple or higher order. This way one varies the focal distance or the position of the focal point vis-a-vis the equipment. The same effect obtains when the coupling body 8" is made of different materials, or that the material is inhomogeneously distributed.

Without any further particularization in the internal set up and construction of the coupling member 8" the shock waves as indicated by lines 21a and 21b will be focused in 15. However, through the special contouring of coupling member 8" the focal point may be shifted to a new focalpoint 15" as indicated by the lines 22a and 22b. This shifting of course has the purpose of permitting focusing right in the kidney stone 16" without having to move the equipment away from the body such displacement of course would generate a gap between whatever coupling body is used and the body 18 of the patient. Decisive is the general aspect that it cannot possibly be expected that a particular concrement such as 16 or 16" has always the same distance from the skin of the patient. Thus the particular embodiment of FIG. 3 permits direct and immediate adaptation of the equipment to the particular situation and here the particular location of the kidney stone 16" not only within the kidney 17" but within the body 18 generally. Owing to this particular configuration and here the curvature of the surface 20 indeed a focal point shift occurs from the lines 21b and 21a to the cone 22a and 22b delineating in fact a hypothetical surface of a cone of wider apex angle. As stated above another possibility in modifying the focal point is to change the membrane 4 and here particularly its curvature or by causing the cone angle of cavity 6 to differ such that the apex of the cone no longe coincides with the center of the sphere outlined by the membrane 4 which in this case remains invariant.

In lieu of a hyperboloid configuration of the surface 20 one may, as indicated in dashed lines 23, provide a more or less concentrical spherical-calotte surface which serves as special boundary between coupling body 8" and the cavity 6. This means that the difference in acousitc properties of the content of cavity 6 and of the material of body or member 8" no longer has the effect of causing a refraction of the shock wave propagation because the shock wavefront hits the surface 23 at right angles everywhere so that the change in discontinuity is no longer effective.

The invention is not limited to the embodiments described above but all changes and modifications thereof, not constituting departures from the spirit and scope of the invention, are intended to be included.

I claim:

1. A device for contactless comminution of concrements in the body of living beings including a casing with a hollow interior and cavity filled with a shock wave transmitting medium and having an internal surface being spherical-calotte shaped and serving as support for an electric coil there being a correspondingly curved insulation on the coil and a metallic membrane of correspondingly calotte shaped configuration held on said insulation layer, there being means for providing an electric current pulse or pulses to said coil the improvement comprising:

said cavity having in addition a boundary surface being configured as a truncated cone and extending from an edge zone of the calotte shaped surface and wherein a center of curvature of said membrane coincides with the apex of said cone, in combination with a covering enclosure and coupling member for said cavity providing coupling function to be placed in abutment with the body of said human being.

2. The improvement as in claim 1 wherein the casing portion delineating said truncated cone at least in the immediate vicinity thereof is made of a material with high acoustic impedance.

3. The improvement as in claim 2 said material being stainless steel.

4. The improvement as in claim 1 wherein said cavity is filled with a pressurized medium said medium having a nonlinear compressibility.

5. The improvement as in claim 4 said medium being water.

6. The improvement as in claim 4 said medium having a low modulus of shear or torsion.

7. The improvement as in claim 6 said medium being rubber elastic body.

8. The improvement as in claim 1 wherein said coupling member has a low modulus of shear or torsion.

9. The improvement as in claim 8 wherein said coupling member is a rubber elastic material.

10. The improvement as in claim 1 wherein said coupling member modifies focusing of shock waves produced by the membrane.

11. The improvement as in claim 10 said coupling member where facing said cavity having a surface of rotational symmetry and hyperboloid configuration.

12. The improvement as in claim 1 wherein said coupling member has a surface facing the cavity being concentric with said membrane.

13. The improvement as in claim 1 wherein said coupling member at least partially projects into that cavity.

* * * * *